United States Patent [19]

Uthemann et al.

[11] Patent Number: 4,770,856

[45] Date of Patent: Sep. 13, 1988

[54] MICROTITER PLATE FOR BLOOD TYPING

[75] Inventors: Horst Uthemann; Dieter Merz; Hans Schleussner, all of Frankfurt, Fed. Rep. of Germany

[73] Assignee: Biotest-Serum-Institut GmbH, Frankfurt, Fed. Rep. of Germany

[21] Appl. No.: 114,891

[22] Filed: Oct. 29, 1987

Related U.S. Application Data

[63] Continuation of Ser. No. 853,571, Jul. 18, 1986, abandoned, which is a continuation-in-part of Ser. No. 454,312, Dec. 29, 1982, abandoned.

[30] Foreign Application Priority Data

Dec. 28, 1981 [DE] Fed. Rep. of Germany ... 8137962[U]

[51] Int. Cl.$^4$ .................... G01N 21/03; G01N 33/48; G01N 33/50
[52] U.S. Cl. .................... 422/104; 422/22; 422/41; 422/57; 422/58; 422/99; 422/102; 422/906; 422/907; 436/165; 436/531; 436/532; 436/809; 435/180; 435/293; 435/300; 435/301; 427/40; 427/41
[58] Field of Search .................. 422/61, 99, 100, 101, 422/102, 104, 40, 41, 285, 22, 23, 906, 907, 57, 58; 436/807, 808, 809, 810, 531, 532, 533, 165; 435/293, 297, 298, 300, 301, 180, 173; 427/40, 41

[56] References Cited

U.S. PATENT DOCUMENTS

| | | | |
|---|---|---|---|
| 3,646,346 | 2/1972 | Catl | 422/57 |
| 4,009,037 | 2/1977 | Mann et al. | 427/40 |
| 4,079,393 | 3/1978 | Marachy et al. | 356/39 |
| 4,154,795 | 5/1979 | Thorne | 422/99 |
| 4,284,725 | 8/1981 | Fennel, III et al. | 422/99 |
| 4,337,104 | 6/1982 | Lynn | 427/40 |
| 4,613,317 | 9/1986 | Williams et al. | 427/41 |

OTHER PUBLICATIONS

Costar Catalogue 3596 (1981).

Primary Examiner—Barry S. Richman
Assistant Examiner—Lynn Kummert
Attorney, Agent, or Firm—Sprung Horn Kramer & Woods

[57] ABSTRACT

A microtiter plate for blood typing consisting of a flat-bottomed plate of rigid transparent polystyrene having a plurality of wells, the polystyrene being surface treated by a corona and/or plasma method of applying high power electric energy at high frequency resulting in a permanently measurable negative ion-charge at the surface of the wells, and layers of substantially pure antiserums dried on the wells without any binder from a suspension or solution of the antiserums and tightly but releasably bound to the polystryene.

6 Claims, 1 Drawing Sheet

MICROTITER PLATE FOR BLOOD TYPING

This is a continuation of application Ser. No. 853,571, filed July 18, 1986, abandoned which is a continuation-in-part of Ser. No. 454,312, filed Dec. 29, 1982, abandoned.

The invention relates to a microtiter plate for blood typing.

Microtiter plates of this type are used for blood-group serology in blood banks and hospitals and to determine paternity. The microdetermination of blood groups is described in 1. Crawford, M. N., Gottman, F. E., and Gottman, C. A., Microplate system for routine use in blood bank laboratories, Transfusion 10, 258–63 (1970),
2. Parker, J. L., Marcous, D. A., Hafleigh, E. B., and Grumet, F. C., Modified microtiter tray method for blood typing, Transfusion 18, 417–22 (1978),
3. Lapinski, F. J., Crowley, K. M., Merrit, C. A., and Henry, J. B., Use of microplate methods in paternity testing, Amer. Soc. Clin. Path. 70, 766–69 (1978),
4. Depew, K. A., Balk, J. W., Meiers, J., and Schorr, J. B., Adaptation of the microtiter technique for use in a blood bank laboratory, AABB, Atlanta, Nov. 1977,
5. Warlow A. and Tills D., Micromethods in blood group serology, Vox Sanguinis 35, 354–56 (1978), and
6. American Red Cross: Application of microplates in regional blood centers, National Headquarters, Washington, D.C.

The micromethod has certain advantages over existing methods like spot-plating, tube centrifuging, or slide testing, namely lower cost, less time, suitability for routine use, and greater sensitivity.

Reference (2) described flexible microtiter plates of PVC with V-shaped wells, (1) and (3) rigid microtiter plates of polystyrene with U-shaped wells, and (5) what are called Terasaki plates. They are used for testing in the ABO, Rh, and other systems and may include anti-human globulin testing as well. Serum tests are also described.

Although these methods employing microtiter plates represent an improvement over existing methods, they all involve either placing liquid antiserums in the wells immediately before testing or storing and freezing them.

The placement of the liquid antiserums on site or for freezing takes a relatively long time and is difficult. A series of antiserum containers must always be available. Furthermore, certain antiserums do not have a very satisfactory shelf life in the liquid state. Finally, pipettes must be employed to place the antiserums.

Reference (2) also mentions problems with liquid antiserums like electrostatic charging of the plates that makes the material cling to the walls.

It is accordingly an object of the invention to provide a microtiter plate that will considerably simplify and extensively automate blood typing.

This object is realized in accordance with the invention pursuant to which there is provided a microtiter plate for blood typing consisting of a flat-bottomed plate of rigid transparent polystyrene having a plurality of wells, the polystyrene being surface treated by a corona and/or plasma method of applying high power electric energy at high frequency resulting in a permanently measurable negative ion-charge at the surface of the wells, and layers of substantially pure antiserums dried on the wells without any binder from a suspension or solution of the antiserums and tightly but releasably bound to the polystyrene.

Blood-typing cards made of polyester film with a layer of pigment-lacquer-matting and surfaced with a layer of dry Antiserum A and B are known from German Utility Model No. 8 029 596.

It has, surprisingly, been discovered that antiserums bind extremely well to rigid, transparent polystyrene surfaces treated as hereinabove set forth without any additives or binders to promote adhesion. Antiserums form a tightly adhesive layer on the bottom of the wells when, for example, a drop of solution or suspension containing the antiserum is placed in a well followed by evaporation of the liquid. The simulation of shipping conditions has not loosened the layer. Ready-to-use microtiter plates coated with dried antiserum and that do not therefore have to be filled with liquid antiserums have been prepared in accordance with the invention. No rehydration is necessary before use. It is only necessary to add a drop of sodium chloride suspension to the blood being tested in order to release the antiserums by a slight shaking. The sample can be shaken up and evaluated after brief centrifuging (2 minutes at 1000 U/min for example).

Especially appropriate microtiter plates are those with U-shaped or flat bottomed, cylindrical-walled wells, although even V-shaped wells are practical. Also especially useful as plates are radiation-sterilized polystyrene.

Like known microtiter plates, these plates have a number of wells ranged longitudinally and transversely next to each other in one plane. This makes it possible to combine serum and antiserum in many ways.

The plates or wells in accordance with the invention are at least coated with antiserums for blood typing in the ABO and Rh systems. Antiserums in the ABO system are distinguished by high avidity, whereas chemically modified antiserums (like Anti-D or Anti-CDE), which also agglutinate rapidly in a sodium chloride environment, are employed for the Rh system.

Since chemically modified IgG molecules, with disulfide bridges in the hinge region to some extent reductively separated and alkylated, are distinguished by high flexibility, the conventional addition of supplements such as protein, dextran, gelatin, AB serum, etc. is not necessary for antiserums based thereon. Chemical modification converts incomplete antibodies into agglutinins that have properties similar to ABO test serums. Thus, modified IgG with anti-D specificity agglutinates $D(Rh_o)$-positive erythrocytes in a sodium chloride solution or in a compatible serum or plasma.

Pirofsky, B. and Cordova, M. S., Bivalent nature of incomplete anti-$D(Rh_o)$, Nature 197, pp. 392–93 (1963) and Roman, D., Tilley, C. A., Crookstone, N. C., Falk, R. E., and Dorington, K. J., Conversion of incomplete antibodies to direct agglutinins by mild reduction. Evidence for segmental flexibility within the $F_c$ fragment of immune globuline G, Proc. Natl. Acad. Sci., U.S.A. 74, pp. 2531–35 (1977)

describe this anti-D reagent. The rapid slide test, slide incubation test and tube contrifugation test have been previously proposed as applications.

It has, surprisingly, been discovered that anti-D reagent, dried on the bottom of a surface-treated polystyrene well and without having to be previously dissolved in water, will supply agglutination pictures that are comparable in strength to the ABO system when agitated with D(Rh$_o$)-positive blood at a short reaction time (about 1 minute). Because the reagent neither contains supplements nor requires high-polymeric adhesion-promoting additives to dry on the bottom of the wells, no control is necessary. It can hardly be expected and has not been described as yet that anti-D reagent, with its low concentration of protein, which corresponds to the concentration in normal human serum, could lead to the false positive reactions with IgG- and/or complement-charged erythrocytes in autoimmune diseases or erythroblastosis of the newborn that have frequently been observed with incomplete anti-Rh serums that contain bovine albumin or other high-molecular substances.

In addition to the ABO and Rh systems like anti-D and anti-CDE, the plates are very practical when coated with anti-AB, AB-serum, anti-Kell, and other systems. The plates should accordingly have enough wells to provide for layers of any desired system. At least seven or eight wells should be made laterally. Commercially available plates have 96 wells, with 8 across and 12 longitudinally.

To prevent mixups the antiserum layers can be differently colored.

In one preferred system, the bottom of one well is coated with antiserum A, the bottom of another with antiserum B, the bottom of another with antiserum AB, the bottom of another with AB serum, the bottom of another with IgG specific to anti-D, and the bottom of another with IgG specific to anti-CDE.

In another system, the bottom of the wells independently contain at least two different antisera and each different antiserum is of a different color.

The ready-to-use plates are individually bonded into aluminum envelopes and stored at 2°-8° C.

The invention will now be specified with references to the accompanying drawings wherein.

Figure 1:
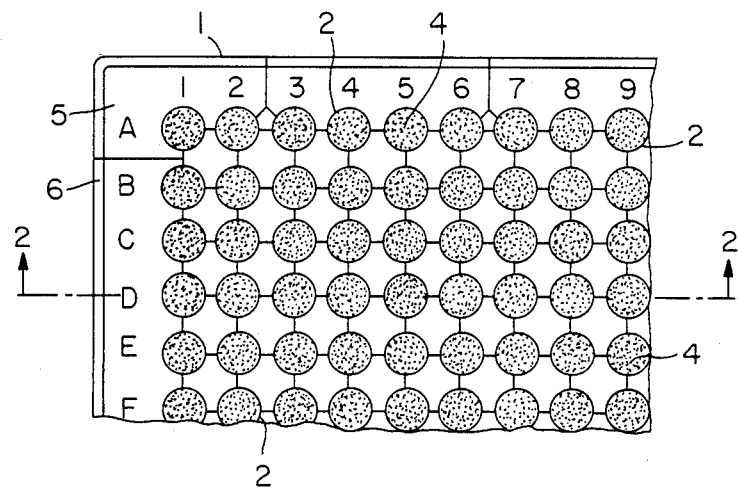
FIG. 1 is a top plan view of a plate in accordance with the invention.

Referring now more particularly to the drawing, in FIG. 1 there is shown a flat-bottomed plate 1 with a number of adjacent cylindrical wells 2 with bottoms coated with a layer 4 of antiserum. In the embodiment illustrated, the whole series of depressions is surrounded by a frame 5 and a shelf 6 on which a cover rests. The individual depressions in one row are designated or identified by the letters A, B, C, etc. and those in one column with the numbers 1, 2, 3, etc.

Figure 2:
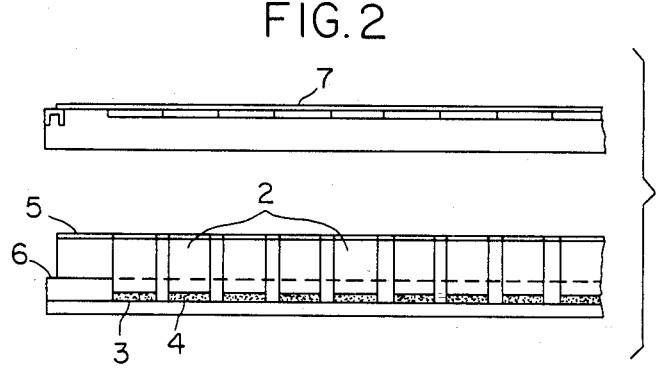
FIG. 2 is an exploded schematic sectional view taken along line A—A of FIG. 1.

FIG. 2 shows the cylindrical wells 2 each with its bottom 3 and layer 4 of antiserum surrounded by frame 5 and shelf 6 on which a cover 7 rests.

It will be understood that the specification and examples are illustrative but not limitative of the present invention and that other embodiments within the spirit and scope of the invention will suggest themselves to those skilled in the art.

We claim:

1. A microtiter plate for blood typing consisting of a flat-bottomed plate of rigid transparent polystyrene having a plurality of wells, and polystyrene being surface treated by a corona and/or plasma method of applying high power electric energy at high frequency resulting in a permanently measurable negative ion-charge at the surface of the wells, and layers of substantially pure antiserums dried on the wells without any binder from a suspension or solution of the antiserums and tightly but releasably bound to the polystyrene.

2. A plate according to claim 1, wherein the wells are U-shaped.

3. A place according to claim 1, wherein the wells are cylindrical.

4. A plate according to claim 1, wherein the polystyrene has been radiation-sterilized.

5. A plate according to claim 1, wherein the bottom of one well is coated with antiserum A, the bottom of another with antiserum B, the bottom of another with antiserum AB, the bottom of another with AB serum, the bottom of another with IgG specific to anti-D, and the bottom of another with IgG specific to anti-CDE.

6. A plate according to claim 1, wherein the bottom of the wells independently contain at least two different antisera and each different antiserum is of a different color.

* * * * *

UNITED STATES PATENT AND TRADEMARK OFFICE
CERTIFICATE OF CORRECTION

PATENT NO. : 4,770,856
DATED : September 13, 1988
INVENTOR(S) : Horst Uthemann, et al It is certified that error appears in the above-identified patent and that said Letters Patent is hereby corrected as shown below:

Title Page, under "U.S. Patent Documents", Line 1, delete "Catl" and substitute --Catt--;
Line 7, delete "4,613,317" and substitute --4,613,517--

Col. 1, line 36 Delete "described" and substitute --describes--

Col. 4, line 29 Delete "place" and substitute --plate--

Signed and Sealed this

Eleventh Day of April, 1989

Attest:

DONALD J. QUIGG

*Attesting Officer*  *Commissioner of Patents and Trademarks*